United States Patent
Li et al.

(10) Patent No.: US 9,144,658 B2
(45) Date of Patent: Sep. 29, 2015

(54) MINIMIZING IMPOSED EXPIRATORY RESISTANCE OF MECHANICAL VENTILATOR BY OPTIMIZING EXHALATION VALVE CONTROL

(75) Inventors: Kun Li, San Diego, CA (US);
Periagounder Arul, Irvine, CA (US);
Gabriel Sanchez, Valley Center, CA (US)

(73) Assignee: COVIDIEN LP, Mansfield, MA (US)

( * ) Notice: Subject to any disclaimer, the term of this patent is extended or adjusted under 35 U.S.C. 154(b) by 694 days.

(21) Appl. No.: 13/459,800

(22) Filed: Apr. 30, 2012

(65) Prior Publication Data

US 2013/0284177 A1 Oct. 31, 2013

(51) Int. Cl.
| | | |
|---|---|---|
| *A61M 16/20* | (2006.01) | |
| *A61B 5/08* | (2006.01) | |
| *A61M 16/00* | (2006.01) | |
| *A61M 16/08* | (2006.01) | |
| *A61M 16/04* | (2006.01) | |

(52) U.S. Cl.
CPC ............ *A61M 16/20* (2013.01); *A61M 16/0051* (2013.01); *A61M 16/0866* (2014.02); *A61M 16/205* (2014.02); *A61M 16/04* (2013.01); *A61M 2016/0027* (2013.01); *A61M 2016/0042* (2013.01); *A61M 2205/505* (2013.01)

(58) Field of Classification Search
CPC ............ A61M 16/20; A61M 16/0051; A61M 16/205; A61M 16/0866; A61M 16/00; A61M 16/0012; A61M 16/204; A61M 16/0009; A61M 16/0054; A61M 16/0069; A61M 16/0666; A61M 16/04; A61M 16/0057; A61M 16/0875; A61M 16/206; A61M 16/0006; A61M 16/0066; A61M 16/06; A61M 16/0816; A61M 16/125; A61M 16/161; A61B 5/085; A61B 5/7239; A62B 9/02
USPC ............ 128/205.24, 200.24, 204.18, 204.21, 128/204.23, 204.26, 204.28, 205.11, 128/204.25, 913, 203.12, 204.27, 203.14, 128/205.19
See application file for complete search history.

(56) References Cited

U.S. PATENT DOCUMENTS

| | | | |
|---|---|---|---|
| 3,444,857 | A | 5/1969 | Godel |
| 3,481,333 | A | 12/1969 | Garrison |
| 3,485,243 | A | 12/1969 | Bird et al. |
| 3,688,794 | A | 9/1972 | Bird et al. |
| 4,241,756 | A | 12/1980 | Bennett et al. |
| 4,527,557 | A | 7/1985 | DeVries et al. |
| 4,608,976 | A | 9/1986 | Suchy |
| 4,699,137 | A | 10/1987 | Schroeder |
| RE32,553 | E | 12/1987 | Bennett et al. |

(Continued)

FOREIGN PATENT DOCUMENTS

WO    WO 2007/102866    9/2007

OTHER PUBLICATIONS

7200 Series Ventilator, Options, and Accessories: Operator's Manual. Nellcor Puritan Bennett, Part No. 22300 A, Sep. 1990, pp. 1-196.

(Continued)

*Primary Examiner* — Annette Dixon
(74) *Attorney, Agent, or Firm* — Merchant & Gould P.C.

(57) ABSTRACT

This disclosure describes systems and methods for controlling an exhalation valve based on pressure and/or flow measurements during exhalation. The disclosure describes novel exhalation valve controls for ventilating a patient.

16 Claims, 7 Drawing Sheets

(56) References Cited

U.S. PATENT DOCUMENTS

| | | | |
|---|---|---|---|
| 4,712,580 A | 12/1987 | Gilman et al. | |
| 4,727,871 A | 3/1988 | Smargiassi et al. | |
| 4,752,089 A | 6/1988 | Carter | |
| 4,921,642 A | 5/1990 | LaTorraca | |
| 4,954,799 A | 9/1990 | Kumar | |
| 4,957,107 A | 9/1990 | Sipin | |
| 4,991,576 A | 2/1991 | Henkin et al. | |
| 4,993,269 A | 2/1991 | Guillaume et al. | |
| 5,000,173 A | 3/1991 | Zalkin et al. | |
| 5,020,532 A | 6/1991 | Mahoney et al. | |
| 5,057,822 A | 10/1991 | Hoffman | |
| 5,072,729 A | 12/1991 | DeVries | |
| 5,072,737 A | 12/1991 | Goulding | |
| 5,109,838 A | 5/1992 | Elam | |
| 5,127,400 A | 7/1992 | DeVries et al. | |
| 5,134,995 A | 8/1992 | Gruenke et al. | |
| 5,150,291 A | 9/1992 | Cummings et al. | |
| 5,161,525 A | 11/1992 | Kimm et al. | |
| 5,168,868 A | 12/1992 | Hicks | |
| 5,178,155 A | 1/1993 | Mault | |
| 5,237,987 A | 8/1993 | Anderson et al. | |
| 5,255,675 A | 10/1993 | Kolobow | |
| 5,259,373 A | 11/1993 | Gruenke et al. | |
| 5,269,293 A | 12/1993 | Loser et al. | |
| 5,271,389 A | 12/1993 | Isaza et al. | |
| 5,277,175 A | 1/1994 | Riggs et al. | |
| 5,279,549 A | 1/1994 | Ranford | |
| 5,299,568 A | 4/1994 | Forare et al. | |
| 5,301,667 A | 4/1994 | McGrail et al. | |
| 5,301,921 A | 4/1994 | Kumar | |
| 5,303,699 A | 4/1994 | Bonassa et al. | |
| 5,309,901 A | 5/1994 | Beaussant | |
| 5,319,540 A | 6/1994 | Isaza et al. | |
| 5,325,861 A | 7/1994 | Goulding | |
| 5,331,995 A | 7/1994 | Westfall et al. | |
| 5,333,606 A | 8/1994 | Schneider et al. | |
| 5,339,807 A | 8/1994 | Carter | |
| 5,343,857 A | 9/1994 | Schneider et al. | |
| 5,343,858 A | 9/1994 | Winefordner et al. | |
| 5,351,522 A | 10/1994 | Lura | |
| 5,357,946 A | 10/1994 | Kee et al. | |
| 5,368,019 A | 11/1994 | LaTorraca | |
| 5,368,021 A | 11/1994 | Beard et al. | |
| 5,383,449 A | 1/1995 | Forare et al. | |
| 5,385,142 A | 1/1995 | Brady et al. | |
| 5,390,666 A | 2/1995 | Kimm et al. | |
| 5,398,677 A | 3/1995 | Smith | |
| 5,401,135 A | 3/1995 | Stoen et al. | |
| 5,402,796 A | 4/1995 | Packer et al. | |
| 5,407,174 A | 4/1995 | Kumar | |
| 5,413,110 A | 5/1995 | Cummings et al. | |
| 5,438,980 A | 8/1995 | Phillips | |
| 5,443,075 A | 8/1995 | Holscher | |
| 5,452,714 A | 9/1995 | Anderson et al. | |
| 5,467,766 A | 11/1995 | Ansite et al. | |
| 5,484,270 A | 1/1996 | Adahan | |
| 5,494,028 A | 2/1996 | DeVries et al. | |
| 5,497,767 A | 3/1996 | Olsson et al. | |
| 5,503,140 A | 4/1996 | Winefordner et al. | |
| 5,513,631 A | 5/1996 | McWilliams | |
| 5,517,983 A | 5/1996 | Deighan et al. | |
| 5,520,071 A | 5/1996 | Jones | |
| 5,524,615 A | 6/1996 | Power | |
| 5,531,221 A | 7/1996 | Power | |
| 5,540,220 A | 7/1996 | Gropper et al. | |
| 5,542,415 A | 8/1996 | Brady | |
| 5,542,416 A | 8/1996 | Chalvignac | |
| 5,544,674 A | 8/1996 | Kelly | |
| 5,546,935 A | 8/1996 | Champeau | |
| 5,549,106 A | 8/1996 | Gruenke et al. | |
| 5,568,910 A | 10/1996 | Koehler et al. | |
| 5,572,993 A * | 11/1996 | Kurome et al. | 128/204.23 |
| 5,575,283 A | 11/1996 | Sjoestrand | |
| 5,596,984 A | 1/1997 | O'Mahoney et al. | |
| 5,606,968 A | 3/1997 | Mang | |
| 5,617,847 A | 4/1997 | Howe | |
| 5,630,411 A | 5/1997 | Holscher | |
| 5,632,270 A | 5/1997 | O'Mahony et al. | |
| 5,645,048 A | 7/1997 | Brodsky et al. | |
| 5,657,750 A | 8/1997 | Colman et al. | |
| 5,660,171 A | 8/1997 | Kimm et al. | |
| 5,662,099 A | 9/1997 | Tobia et al. | |
| 5,664,560 A | 9/1997 | Merrick et al. | |
| 5,664,562 A | 9/1997 | Bourdon | |
| 5,671,767 A | 9/1997 | Kelly | |
| 5,672,041 A | 9/1997 | Ringdahl et al. | |
| 5,673,689 A | 10/1997 | Power | |
| 5,678,537 A | 10/1997 | Bathe et al. | |
| 5,683,232 A | 11/1997 | Adahan | |
| 5,692,497 A | 12/1997 | Schnitzer et al. | |
| 5,697,363 A | 12/1997 | Hart | |
| 5,701,883 A | 12/1997 | Hete et al. | |
| 5,701,889 A | 12/1997 | Danon | |
| 5,715,812 A | 2/1998 | Deighan et al. | |
| 5,762,480 A | 6/1998 | Adahan | |
| 5,771,884 A | 6/1998 | Yarnall et al. | |
| 5,791,339 A | 8/1998 | Winter | |
| 5,794,614 A | 8/1998 | Gruenke et al. | |
| 5,794,986 A | 8/1998 | Gansel et al. | |
| 5,797,393 A | 8/1998 | Kohl | |
| 5,803,064 A | 9/1998 | Phelps et al. | |
| 5,813,399 A | 9/1998 | Isaza et al. | |
| 5,823,179 A | 10/1998 | Grychowski et al. | |
| 5,826,575 A | 10/1998 | Lall | |
| 5,829,441 A | 11/1998 | Kidd et al. | |
| 5,845,636 A | 12/1998 | Gruenke et al. | |
| 5,857,458 A | 1/1999 | Tham et al. | |
| 5,864,938 A | 2/1999 | Gansel et al. | |
| 5,865,168 A | 2/1999 | Isaza | |
| 5,868,133 A | 2/1999 | DeVries et al. | |
| 5,875,783 A | 3/1999 | Kullik | |
| 5,876,352 A | 3/1999 | Weismann | |
| 5,881,717 A | 3/1999 | Isaza | |
| 5,881,722 A | 3/1999 | DeVries et al. | |
| 5,881,723 A | 3/1999 | Wallace et al. | |
| 5,884,623 A | 3/1999 | Winter | |
| 5,909,731 A | 6/1999 | O'Mahony et al. | |
| 5,915,379 A | 6/1999 | Wallace et al. | |
| 5,915,380 A | 6/1999 | Wallace et al. | |
| 5,915,382 A | 6/1999 | Power | |
| 5,918,597 A | 7/1999 | Jones et al. | |
| 5,921,238 A | 7/1999 | Bourdon | |
| 5,934,274 A | 8/1999 | Merrick et al. | |
| 5,937,856 A | 8/1999 | Jonasson et al. | |
| 5,941,846 A | 8/1999 | Duffy et al. | |
| 5,957,130 A | 9/1999 | Krahbichler et al. | |
| 6,024,089 A | 2/2000 | Wallace et al. | |
| 6,041,777 A | 3/2000 | Faithfull et al. | |
| 6,041,780 A | 3/2000 | Richard et al. | |
| 6,047,860 A | 4/2000 | Sanders | |
| 6,073,630 A | 6/2000 | Adahan | |
| 6,076,523 A | 6/2000 | Jones et al. | |
| 6,095,139 A | 8/2000 | Psaros | |
| 6,102,038 A | 8/2000 | DeVries | |
| 6,116,240 A | 9/2000 | Merrick et al. | |
| 6,116,464 A | 9/2000 | Sanders | |
| 6,119,686 A | 9/2000 | Somerson et al. | |
| 6,123,073 A | 9/2000 | Schlawin et al. | |
| 6,123,074 A | 9/2000 | Hete et al. | |
| 6,131,571 A | 10/2000 | Lampotang et al. | |
| 6,135,106 A | 10/2000 | Dirks et al. | |
| 6,135,967 A | 10/2000 | Fiorenza et al. | |
| 6,142,150 A | 11/2000 | O'Mahony | |
| 6,148,814 A | 11/2000 | Clemmer et al. | |
| 6,152,132 A | 11/2000 | Psaros | |
| 6,152,135 A | 11/2000 | DeVries et al. | |
| 6,158,432 A | 12/2000 | Biondi et al. | |
| 6,161,539 A | 12/2000 | Winter | |
| 6,176,234 B1 | 1/2001 | Salter et al. | |
| 6,192,885 B1 | 2/2001 | Jalde | |
| 6,217,524 B1 | 4/2001 | Orr et al. | |
| 6,220,245 B1 | 4/2001 | Takabayashi et al. | |
| 6,269,812 B1 | 8/2001 | Wallace et al. | |
| 6,273,444 B1 | 8/2001 | Power | |

(56) References Cited

U.S. PATENT DOCUMENTS

| | | |
|---|---|---|
| 6,283,119 B1 | 9/2001 | Bourdon |
| 6,287,264 B1 | 9/2001 | Hoffman |
| 6,295,330 B1 | 9/2001 | Skog et al. |
| 6,295,985 B1 | 10/2001 | Kock et al. |
| 6,305,373 B1 | 10/2001 | Wallace et al. |
| 6,306,098 B1 | 10/2001 | Orr et al. |
| 6,308,706 B1 | 10/2001 | Lammers et al. |
| 6,309,360 B1 | 10/2001 | Mault |
| 6,321,748 B1 | 11/2001 | O'Mahoney |
| 6,325,785 B1 | 12/2001 | Babkes et al. |
| 6,349,922 B1 | 2/2002 | Rydin |
| 6,357,438 B1 | 3/2002 | Hansen |
| 6,360,745 B1 | 3/2002 | Wallace et al. |
| 6,369,838 B1 | 4/2002 | Wallace et al. |
| 6,371,113 B1 | 4/2002 | Tobia et al. |
| 6,412,483 B1 | 7/2002 | Jones et al. |
| 6,415,788 B1 | 7/2002 | Clawson et al. |
| 6,419,634 B1 | 7/2002 | Gaston, IV et al. |
| 6,439,229 B1 | 8/2002 | Du et al. |
| 6,457,472 B1 | 10/2002 | Schwartz et al. |
| 6,467,478 B1 | 10/2002 | Merrick et al. |
| 6,523,537 B1 | 2/2003 | Mas Marfany |
| 6,523,538 B1 | 2/2003 | Wikefeldt |
| 6,526,970 B2 | 3/2003 | DeVries et al. |
| 6,543,449 B1 | 4/2003 | Woodring et al. |
| 6,546,930 B1 | 4/2003 | Emerson et al. |
| 6,550,479 B1 | 4/2003 | Duxbury |
| 6,553,991 B1 | 4/2003 | Isaza |
| 6,557,553 B1 | 5/2003 | Borrello |
| 6,557,554 B1 | 5/2003 | Sugiura |
| 6,564,798 B1 | 5/2003 | Jalde |
| 6,571,795 B2 | 6/2003 | Bourdon |
| 6,572,561 B2 | 6/2003 | Mault |
| 6,575,164 B1 | 6/2003 | Jaffe et al. |
| 6,575,165 B1 | 6/2003 | Cook et al. |
| 6,575,918 B2 | 6/2003 | Kline |
| 6,584,973 B1 | 7/2003 | Biondi et al. |
| 6,606,994 B1 | 8/2003 | Clark |
| 6,616,615 B2 | 9/2003 | Mault |
| 6,619,289 B1 | 9/2003 | Mashak |
| 6,622,725 B1 | 9/2003 | Fisher et al. |
| 6,622,726 B1 | 9/2003 | Du |
| 6,629,934 B2 | 10/2003 | Mault et al. |
| 6,631,716 B1 | 10/2003 | Robinson et al. |
| 6,644,310 B1 | 11/2003 | Delache et al. |
| 6,668,824 B1 | 12/2003 | Isaza et al. |
| 6,675,801 B2 | 1/2004 | Wallace et al. |
| 6,718,974 B1 | 4/2004 | Moberg |
| 6,722,359 B2 | 4/2004 | Chalvignac |
| 6,723,055 B2 | 4/2004 | Hoffman |
| 6,725,447 B1 | 4/2004 | Gilman et al. |
| 6,729,331 B2 | 5/2004 | Kay |
| 6,739,334 B2 | 5/2004 | Valeij |
| 6,739,337 B2 | 5/2004 | Isaza |
| 6,761,167 B1 | 7/2004 | Nadjafizadeh et al. |
| 6,761,168 B1 | 7/2004 | Nadjafizadeh et al. |
| 6,763,829 B2 | 7/2004 | Jaffe et al. |
| 6,772,762 B2 | 8/2004 | Piesinger |
| 6,805,121 B1 | 10/2004 | Flood et al. |
| 6,814,074 B1 | 11/2004 | Nadjafizadeh et al. |
| 6,866,040 B1 | 3/2005 | Bourdon |
| 6,877,511 B2 | 4/2005 | DeVries et al. |
| 6,886,558 B2 | 5/2005 | Tanaka |
| 6,896,713 B1 | 5/2005 | Eckerbom et al. |
| 6,938,619 B1 | 9/2005 | Hickle |
| 6,960,854 B2 | 11/2005 | Nadjafizadeh et al. |
| 6,968,840 B2 | 11/2005 | Smith et al. |
| 7,032,589 B2 | 4/2006 | Kerechanin, II et al. |
| 7,036,504 B2 | 5/2006 | Wallace et al. |
| 7,040,315 B1 | 5/2006 | Strömberg |
| 7,040,321 B2 | 5/2006 | Göbel |
| 7,043,979 B2 | 5/2006 | Smith et al. |
| 7,066,175 B2 | 6/2006 | Hamilton et al. |
| 7,066,177 B2 | 6/2006 | Pittaway et al. |
| 7,077,131 B2 | 7/2006 | Hansen |
| RE39,225 E | 8/2006 | Isaza et al. |
| 7,117,438 B2 | 10/2006 | Wallace et al. |
| 7,118,537 B2 | 10/2006 | Baddour |
| 7,121,277 B2 | 10/2006 | Ström |
| 7,152,604 B2 | 12/2006 | Hickle et al. |
| 7,168,597 B1 | 1/2007 | Jones et al. |
| 7,195,013 B2 | 3/2007 | Lurie |
| 7,210,478 B2 | 5/2007 | Banner et al. |
| 7,222,623 B2 | 5/2007 | DeVries et al. |
| 7,241,269 B2 | 7/2007 | McCawley et al. |
| 7,270,126 B2 | 9/2007 | Wallace et al. |
| 7,275,540 B2 | 10/2007 | Bolam et al. |
| 7,291,115 B2 | 11/2007 | Cardona Burrul |
| 7,302,949 B2 | 12/2007 | Pelerossi et al. |
| 7,320,321 B2 | 1/2008 | Pranger et al. |
| 7,347,825 B2 | 3/2008 | Vaughan et al. |
| 7,369,757 B2 | 5/2008 | Farbarik |
| 7,370,650 B2 | 5/2008 | Nadjafizadeh et al. |
| 7,392,806 B2 | 7/2008 | Yuen et al. |
| 7,428,902 B2 | 9/2008 | Du et al. |
| 7,460,959 B2 | 12/2008 | Jafari |
| 7,475,685 B2 | 1/2009 | Dietz et al. |
| 7,484,508 B2 | 2/2009 | Younes |
| 7,487,773 B2 | 2/2009 | Li |
| 7,487,778 B2 | 2/2009 | Freitag |
| 7,500,483 B2 | 3/2009 | Colman et al. |
| 7,509,957 B2 | 3/2009 | Duquette et al. |
| 7,525,663 B2 | 4/2009 | Kwok et al. |
| 7,533,670 B1 | 5/2009 | Freitag et al. |
| 7,547,285 B2 | 6/2009 | Kline |
| 7,556,038 B2 | 7/2009 | Kirby et al. |
| 7,556,042 B2 | 7/2009 | West et al. |
| 7,562,657 B2 | 7/2009 | Blanch et al. |
| 7,588,033 B2 | 9/2009 | Wondka |
| 7,610,914 B2 | 11/2009 | Bolam et al. |
| 7,617,824 B2 | 11/2009 | Doyle |
| 7,621,271 B2 | 11/2009 | Brugnoli |
| 7,634,998 B1 | 12/2009 | Fenley |
| 7,654,802 B2 | 2/2010 | Crawford, Jr. et al. |
| 7,694,677 B2 | 4/2010 | Tang |
| 7,699,788 B2 | 4/2010 | Kuck et al. |
| 7,717,113 B2 | 5/2010 | Andrieux |
| 7,721,735 B2 | 5/2010 | Hamilton et al. |
| 7,721,736 B2 | 5/2010 | Urias et al. |
| D618,356 S | 6/2010 | Ross |
| 7,740,591 B1 | 6/2010 | Starr et al. |
| 7,753,052 B2 | 7/2010 | Tanaka |
| 7,779,840 B2 | 8/2010 | Acker et al. |
| 7,784,461 B2 | 8/2010 | Figueiredo et al. |
| 7,810,497 B2 | 10/2010 | Pittman et al. |
| 7,814,908 B2 | 10/2010 | Psaros |
| 7,819,815 B2 | 10/2010 | Younes |
| 7,823,588 B2 | 11/2010 | Hansen |
| 7,828,741 B2 | 11/2010 | Kline et al. |
| 7,846,739 B2 | 12/2010 | von Bahr et al. |
| 7,849,854 B2 | 12/2010 | DeVries et al. |
| 7,855,716 B2 | 12/2010 | McCreary et al. |
| 7,861,716 B2 | 1/2011 | Borrello |
| 7,870,857 B2 | 1/2011 | Dhuper et al. |
| D632,796 S | 2/2011 | Ross et al. |
| D632,797 S | 2/2011 | Ross et al. |
| 7,883,471 B2 | 2/2011 | Aljuri et al. |
| 7,885,771 B2 | 2/2011 | Roecker et al. |
| 7,891,354 B2 | 2/2011 | Farbarik |
| 7,893,560 B2 | 2/2011 | Carter |
| 7,900,626 B2 | 3/2011 | Daly |
| 7,913,690 B2 | 3/2011 | Fisher et al. |
| D638,852 S | 5/2011 | Skidmore et al. |
| 7,984,714 B2 | 7/2011 | Hausmann et al. |
| D643,535 S | 8/2011 | Ross et al. |
| 7,992,557 B2 | 8/2011 | Nadjafizadeh et al. |
| 8,001,967 B2 | 8/2011 | Wallace et al. |
| D645,158 S | 9/2011 | Sanchez et al. |
| 8,021,310 B2 | 9/2011 | Sanborn et al. |
| D649,157 S | 11/2011 | Skidmore et al. |
| D652,521 S | 1/2012 | Ross et al. |
| D652,936 S | 1/2012 | Ross et al. |
| D653,749 S | 2/2012 | Winter et al. |
| 8,113,062 B2 | 2/2012 | Graboi et al. |

(56) References Cited

U.S. PATENT DOCUMENTS

| | | |
|---|---|---|
| D655,405 S | 3/2012 | Winter et al. |
| D655,809 S | 3/2012 | Winter et al. |
| D656,237 S | 3/2012 | Sanchez et al. |
| 8,181,648 B2 | 5/2012 | Perine et al. |
| 8,210,173 B2 | 7/2012 | Vandine |
| 8,210,174 B2 | 7/2012 | Farbarik |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 2002/0026941 A1 | 3/2002 | Biondi et al. |
| 2002/0138213 A1 | 9/2002 | Mault |
| 2003/0062045 A1 | 4/2003 | Woodring et al. |
| 2004/0138577 A1 | 7/2004 | Kline |
| 2004/0261793 A1 | 12/2004 | Stromberg et al. |
| 2005/0039748 A1 | 2/2005 | Andrieux |
| 2005/0098177 A1 | 5/2005 | Haj-Yahya et al. |
| 2005/0139211 A1 | 6/2005 | Alston et al. |
| 2005/0139212 A1 | 6/2005 | Bourdon |
| 2005/0150494 A1 | 7/2005 | DeVries et al. |
| 2005/0217671 A1 | 10/2005 | Fisher et al. |
| 2006/0032499 A1 | 2/2006 | Halsnes |
| 2006/0129054 A1 | 6/2006 | Orr et al. |
| 2006/0130839 A1 | 6/2006 | Bassovitch |
| 2006/0201507 A1 | 9/2006 | Breen |
| 2006/0249148 A1 | 11/2006 | Younes |
| 2006/0249153 A1 | 11/2006 | DeVries et al. |
| 2007/0000494 A1 | 1/2007 | Banner et al. |
| 2007/0017515 A1 | 1/2007 | Wallace et al. |
| 2007/0028921 A1 | 2/2007 | Banner et al. |
| 2007/0062531 A1 | 3/2007 | Fisher et al. |
| 2007/0068530 A1 | 3/2007 | Pacey |
| 2007/0073183 A1 | 3/2007 | Kline |
| 2007/0077200 A1 | 4/2007 | Baker |
| 2007/0095347 A1 | 5/2007 | Lampotang et al. |
| 2007/0113854 A1 | 5/2007 | Mcauliffe |
| 2007/0125377 A1 | 6/2007 | Heinonen et al. |
| 2007/0144521 A1 | 6/2007 | DeVries et al. |
| 2007/0144523 A1 | 6/2007 | Bolam et al. |
| 2007/0157930 A1 | 7/2007 | Soliman et al. |
| 2007/0157931 A1 | 7/2007 | Parker et al. |
| 2007/0163579 A1 | 7/2007 | Li et al. |
| 2007/0227537 A1 | 10/2007 | Bemister et al. |
| 2007/0232952 A1 | 10/2007 | Baddour |
| 2007/0255160 A1 | 11/2007 | Daly |
| 2007/0284361 A1 | 12/2007 | Nadjafizadeh et al. |
| 2008/0045825 A1 | 2/2008 | Melker et al. |
| 2008/0053438 A1 | 3/2008 | DeVries et al. |
| 2008/0053441 A1 | 3/2008 | Gottlib et al. |
| 2008/0060646 A1 | 3/2008 | Isaza |
| 2008/0060656 A1 | 3/2008 | Isaza |
| 2008/0072896 A1 | 3/2008 | Setzer et al. |
| 2008/0072902 A1 | 3/2008 | Setzer et al. |
| 2008/0078390 A1 | 4/2008 | Milne et al. |
| 2008/0083644 A1 | 4/2008 | Janbakhsh et al. |
| 2008/0092894 A1 | 4/2008 | Nicolazzi et al. |
| 2008/0097234 A1 | 4/2008 | Nicolazzi et al. |
| 2008/0135044 A1 | 6/2008 | Freitag et al. |
| 2008/0183094 A1 | 7/2008 | Schonfuss et al. |
| 2008/0196720 A1 | 8/2008 | Kollmeyer et al. |
| 2008/0202517 A1 | 8/2008 | Mitton et al. |
| 2008/0202518 A1 | 8/2008 | Mitton et al. |
| 2008/0214947 A1 | 9/2008 | Hunt et al. |
| 2008/0230062 A1 | 9/2008 | Tham |
| 2008/0257349 A1 | 10/2008 | Hedner et al. |
| 2008/0276939 A1 | 11/2008 | Tiedje |
| 2009/0000621 A1 | 1/2009 | Haggblom et al. |
| 2009/0007914 A1 | 1/2009 | Bateman |
| 2009/0050153 A1 | 2/2009 | Brunner |
| 2009/0056708 A1 | 3/2009 | Stenzler et al. |
| 2009/0056719 A1 | 3/2009 | Newman, Jr. |
| 2009/0071478 A1 | 3/2009 | Kalfon |
| 2009/0078251 A1 | 3/2009 | Zucchi et al. |
| 2009/0084381 A1 | 4/2009 | DeVries et al. |
| 2009/0090359 A1 | 4/2009 | Daviet et al. |
| 2009/0114223 A1 | 5/2009 | Bonassa |
| 2009/0133695 A1 | 5/2009 | Rao et al. |
| 2009/0137919 A1 | 5/2009 | Bar-Lavie et al. |
| 2009/0165795 A1 | 7/2009 | Nadjafizadeh et al. |
| 2009/0171176 A1 | 7/2009 | Andersohn |
| 2009/0188502 A1 | 7/2009 | Tiedje |
| 2009/0205661 A1 | 8/2009 | Stephenson et al. |
| 2009/0205663 A1 | 8/2009 | Vandine et al. |
| 2009/0217923 A1 | 9/2009 | Boehm et al. |
| 2009/0221926 A1 | 9/2009 | Younes |
| 2009/0229612 A1 | 9/2009 | Levi et al. |
| 2009/0235935 A1 | 9/2009 | Pacey |
| 2009/0241948 A1 | 10/2009 | Clancy et al. |
| 2009/0241951 A1 | 10/2009 | Jafari et al. |
| 2009/0241952 A1 | 10/2009 | Nicolazzi et al. |
| 2009/0241953 A1 | 10/2009 | Vandine et al. |
| 2009/0241955 A1 | 10/2009 | Jafari et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0241964 A1 | 10/2009 | Aljuri et al. |
| 2009/0247891 A1 | 10/2009 | Wood |
| 2009/0250054 A1 | 10/2009 | Loncar et al. |
| 2009/0250059 A1 | 10/2009 | Allum et al. |
| 2009/0255533 A1 | 10/2009 | Freitag et al. |
| 2009/0260625 A1 | 10/2009 | Wondka |
| 2009/0263279 A1 | 10/2009 | Kline et al. |
| 2009/0270752 A1 | 10/2009 | Coifman |
| 2009/0277448 A1 | 11/2009 | Ahlmén et al. |
| 2009/0293877 A1 | 12/2009 | Blanch et al. |
| 2009/0299430 A1 | 12/2009 | Davies et al. |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |
| 2010/0011307 A1 | 1/2010 | Desfossez et al. |
| 2010/0012126 A1 | 1/2010 | Gandini |
| 2010/0024820 A1 | 2/2010 | Bourdon |
| 2010/0031961 A1 | 2/2010 | Schmidt |
| 2010/0051026 A1 | 3/2010 | Graboi |
| 2010/0051029 A1 | 3/2010 | Jafari et al. |
| 2010/0059058 A1 | 3/2010 | Kuo |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0078017 A1 | 4/2010 | Andrieux et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0099999 A1 | 4/2010 | Hemnes et al. |
| 2010/0101577 A1 | 4/2010 | Kaestle et al. |
| 2010/0106037 A1 | 4/2010 | Kacmarek et al. |
| 2010/0125227 A1 | 5/2010 | Bird |
| 2010/0137733 A1 | 6/2010 | Wang et al. |
| 2010/0139660 A1 | 6/2010 | Adahan |
| 2010/0147302 A1 | 6/2010 | Selvarajan et al. |
| 2010/0147303 A1 | 6/2010 | Jafari et al. |
| 2010/0170512 A1 | 7/2010 | Kuypers et al. |
| 2010/0175695 A1 | 7/2010 | Jamison |
| 2010/0179392 A1 | 7/2010 | Chang et al. |
| 2010/0180897 A1 | 7/2010 | Malgouyres |
| 2010/0185112 A1 | 7/2010 | Van Kesteren et al. |
| 2010/0186744 A1 | 7/2010 | Andrieux |
| 2010/0198095 A1 | 8/2010 | Isler |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0222692 A1 | 9/2010 | McCawley et al. |
| 2010/0236553 A1 | 9/2010 | Jafari et al. |
| 2010/0236555 A1 | 9/2010 | Jafari et al. |
| 2010/0241019 A1 | 9/2010 | Varga et al. |
| 2010/0242961 A1 | 9/2010 | Mougel et al. |
| 2010/0249584 A1 | 9/2010 | Albertelli |

(56) References Cited

U.S. PATENT DOCUMENTS

| | | |
|---|---|---|
| 2010/0252042 A1 | 10/2010 | Kapust et al. |
| 2010/0268106 A1 | 10/2010 | Johnson et al. |
| 2010/0268131 A1 | 10/2010 | Efthimiou |
| 2010/0269834 A1 | 10/2010 | Freitag et al. |
| 2010/0282258 A1 | 11/2010 | Tailor et al. |
| 2010/0282259 A1 | 11/2010 | Figueiredo et al. |
| 2010/0286544 A1 | 11/2010 | Tanaka et al. |
| 2010/0288283 A1 | 11/2010 | Campbell et al. |
| 2010/0292601 A1 | 11/2010 | Dompeling et al. |
| 2010/0300446 A1 | 12/2010 | Nicolazzi et al. |
| 2010/0324437 A1 | 12/2010 | Freeman et al. |
| 2010/0324439 A1 | 12/2010 | Davenport |
| 2011/0004108 A1 | 1/2011 | Peyton |
| 2011/0009762 A1 | 1/2011 | Eichler et al. |
| 2011/0011400 A1 | 1/2011 | Gentner et al. |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |
| 2011/0041849 A1 | 2/2011 | Chen et al. |
| 2011/0041850 A1 | 2/2011 | Vandine et al. |
| 2011/0066060 A1 | 3/2011 | von Bahr et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132361 A1 | 6/2011 | Sanchez |
| 2011/0132362 A1 | 6/2011 | Sanchez |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0154241 A1 | 6/2011 | Skidmore et al. |
| 2011/0175728 A1 | 7/2011 | Baker, Jr. |
| 2011/0196251 A1 | 8/2011 | Jourdain et al. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0230780 A1 | 9/2011 | Sanborn et al. |
| 2011/0249006 A1 | 10/2011 | Wallace et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |
| 2011/0271960 A1 | 11/2011 | Milne et al. |
| 2011/0273299 A1 | 11/2011 | Milne et al. |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0029317 A1 | 2/2012 | Doyle et al. |
| 2012/0030611 A1 | 2/2012 | Skidmore |
| 2012/0060841 A1 | 3/2012 | Crawford, Jr. et al. |
| 2012/0071729 A1 | 3/2012 | Doyle et al. |
| 2012/0090611 A1 | 4/2012 | Graboi et al. |
| 2012/0096381 A1 | 4/2012 | Milne et al. |
| 2012/0133519 A1 | 5/2012 | Milne et al. |
| 2012/0136222 A1 | 5/2012 | Doyle et al. |
| 2012/0137249 A1 | 5/2012 | Milne et al. |
| 2012/0137250 A1 | 5/2012 | Milne et al. |
| 2012/0167885 A1 | 7/2012 | Masic et al. |
| 2012/0185792 A1 | 7/2012 | Kimm et al. |
| 2012/0197578 A1 | 8/2012 | Vig et al. |
| 2012/0197580 A1 | 8/2012 | Vij et al. |
| 2012/0211008 A1 | 8/2012 | Perine et al. |
| 2012/0216809 A1 | 8/2012 | Milne et al. |
| 2012/0216810 A1 | 8/2012 | Jafari et al. |
| 2012/0216811 A1 | 8/2012 | Kimm et al. |
| 2012/0226444 A1 | 9/2012 | Milne et al. |
| 2012/0247471 A1 | 10/2012 | Masic et al. |
| 2012/0272960 A1 | 11/2012 | Milne |
| 2012/0272961 A1 | 11/2012 | Masic et al. |
| 2012/0272962 A1 | 11/2012 | Doyle et al. |
| 2012/0304995 A1 | 12/2012 | Kauc |
| 2013/0000644 A1 | 1/2013 | Thiessen |
| 2013/0006133 A1 | 1/2013 | Doyle et al. |
| 2013/0006134 A1 | 1/2013 | Doyle et al. |
| 2013/0025596 A1 | 1/2013 | Jafari et al. |
| 2013/0025597 A1 | 1/2013 | Doyle et al. |

OTHER PUBLICATIONS

7200 Ventilatory System: Addendum/Errata. Nellcor Puritan Bennett, Part No. 4-023576-00, Rev. A, Apr. 1988, pp. 1-32.

800 Operator's and Technical Reference Manual. Series Ventilator System, Nellcor Puritan Bennett, Part No. 4-070088-00, Rev. L, Aug. 2010, pp. 1-476.

840 Operator's and Technical Reference Manual. Ventilator System, Nellcor Puritan Bennett, Part No. 4-075609-00, Rev. G, Oct. 2006, pp. 1-424.

DeBlasi, Robert et al., "The Impact of Imposed Expiratory Resistance in Neonatal Mechanical Ventilation: A Laboratory Evaluation", Respiratory Care, Nov. 2008, vol. 53, No. 11, pp. 1450-1460.

* cited by examiner

MINIMIZING IMPOSED EXPIRATORY RESISTANCE OF MECHANICAL VENTILATOR BY OPTIMIZING EXHALATION VALVE CONTROL

INTRODUCTION

Medical ventilator systems have long been used to provide supplemental oxygen support to patients. These ventilators typically comprise a source of pressurized air and oxygen, which is fluidly connected to the patient through a conduit or tubing. The amount of pressure in the gas mixture delivered to the patient may be controlled during ventilation including during inspiration and exhalation.

Patients on a ventilator system are more comfortable when the delivered volume of inspired gas is allowed to be exhaled against the least resistance possible. Generally, resistance is due to the pneumatics of the ventilator, including the tubing, patient interface, exhalation valve, etc., and the respiratory physiology of the patient, including the lungs, bronchiole tubing, etc. Some exhalation modes are designed to open the exhalation valve to the greatest extent possible in order to provide the least amount of resistance to patient exhalation. However, these modes may enable exhalation gases to escape so quickly that the pressure in the patient's lungs falls below a prescribed positive end-expiratory pressure (PEEP). This may endanger the patient by, at best, preventing optimal oxygen exchange, and at worst, allowing alveoli in the lungs to collapse. Alternatively, other exhalation modes are designed to slowly reduce the pressure in the patient tubing to prevent undershoot of the prescribed PEEP, but at the expense of patient comfort.

SUMMARY

This disclosure describes systems and methods for controlling pressure and/or flow during exhalation in order to quickly reduce pressure in the circuit without undershooting PEEP. The disclosure describes novel exhalation modes for ventilating a patient.

In part, this disclosure describes a method for controlling exhalation during ventilation of a patient on a ventilator. The method includes:

a) determining a control command for an exhalation valve, wherein the control command targets a pressure at the exhalation valve between a minimum pressure and a steady-state pressure for a period of time;

b) controlling the exhalation valve based on the control command during one or more exhalation cycles;

c) monitoring an end exhalation pressure and a flow undershoot during the one or more exhalation cycles;

d) comparing the end exhalation pressure to a predetermined pressure range;

e) comparing the flow undershoot to a predetermined flow threshold; and f) based on the comparing, updating the control command in order to maintain a positive-end expiratory pressure (PEEP) at the end of the one or more exhalation cycles.

Yet another aspect of this disclosure describes a ventilator system including:

a) means for determining a control command for an exhalation valve, wherein the control command targets a pressure at the exhalation valve between a minimum pressure and a steady-state pressure for a period of time;

b) means for controlling the exhalation valve based on the control command during one or more exhalation cycles;

c) means for monitoring an end exhalation pressure and a flow undershoot during the one or more exhalation cycles;

d) means for comparing the end exhalation pressure to a predetermined pressure range;

e) means for comparing the flow undershoot to a predetermined flow threshold; and f) based on the comparing, means for updating the control command in order to maintain a positive-end expiratory pressure (PEEP) at the end of the one or more exhalation cycles.

The disclosure further describes a computer-readable medium having computer-executable instructions for performing a method controlling exhalation during ventilation of a patient on a ventilator. The method includes:

a) determining a control command for an exhalation valve, wherein the control command targets a pressure at the exhalation valve between a minimum pressure and a steady-state pressure for a period of time;

b) repeatedly controlling the exhalation valve based on the control command during one or more exhalation cycles;

c) repeatedly monitoring an end exhalation pressure and a flow undershoot during the one or more exhalation cycles;

d) repeatedly comparing the end exhalation pressure to a predetermined pressure range;

e) repeatedly comparing the flow undershoot to a predetermined flow threshold; and f) based on the comparing, repeatedly updating the control command in order to maintain a positive-end expiratory pressure (PEEP) at the end of the one or more exhalation cycles.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the disclosure as claimed.

BRIEF DESCRIPTION OF THE FIGURES

The following drawing figures, which form a part of this application, are illustrative of embodiments, systems and methods described below and are not meant to limit the scope of the invention in any manner, which scope shall be based on the claims appended hereto.

DETAILED DESCRIPTION

Figure 1:
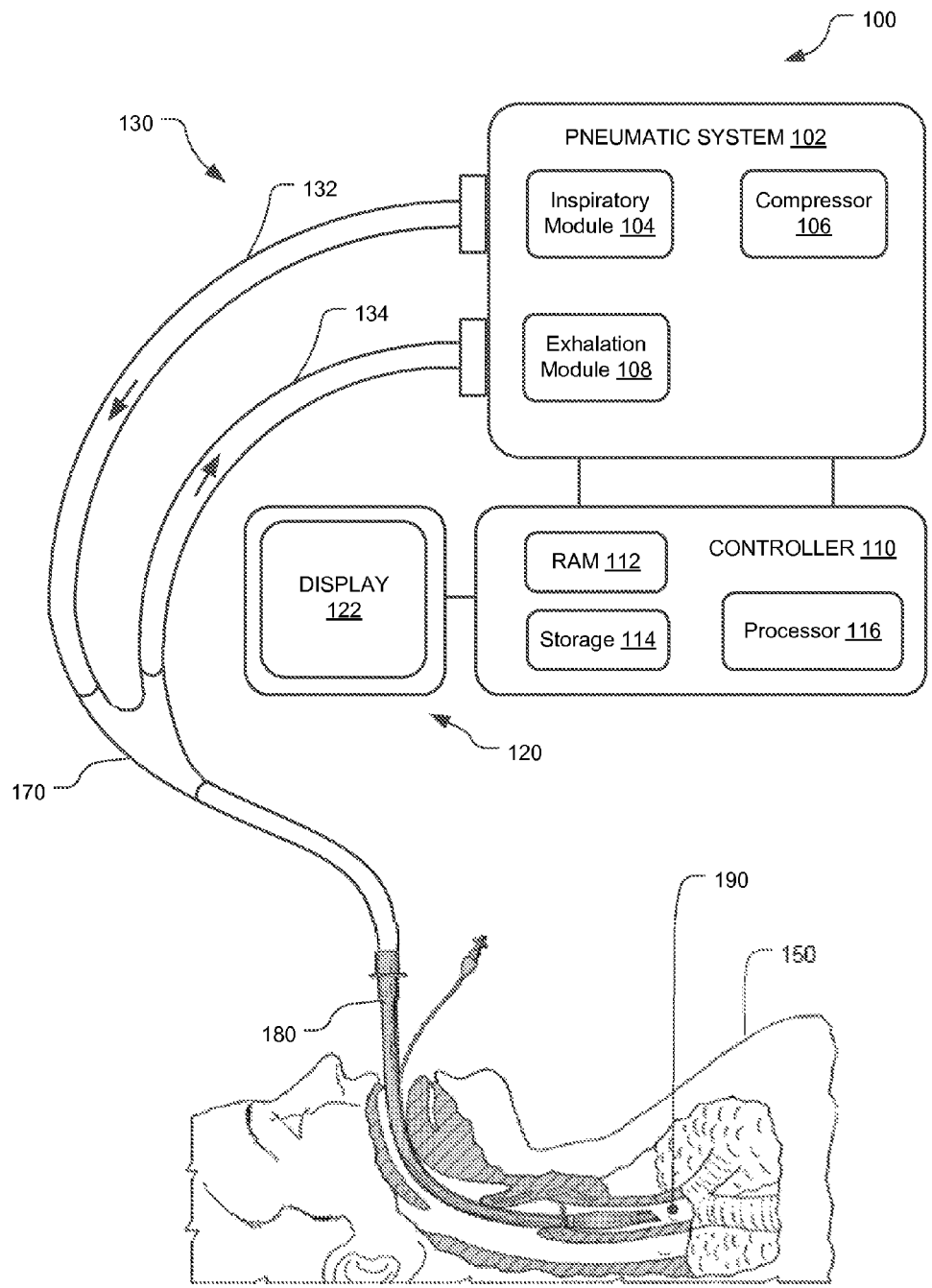
FIG. 1 is a schematic block diagram illustrating one embodiment of a ventilator.

Although the techniques introduced above and discussed in detail below may be implemented for a variety of medical devices, the present disclosure will discuss the implementation of these techniques in the context of a medical ventilator for use in providing ventilation support to a human patient. The reader will understand that the technology described in the context of a medical ventilator for human patients could be adapted for use with other systems, such as ventilators for non-human patients and general gas transport systems.

Medical ventilators are used to provide a breathing gas to a patient who may otherwise be unable to breathe sufficiently. In modern medical facilities, pressurized air and oxygen sources are often available from wall outlets. Accordingly, ventilators may provide pressure regulating valves (or regulators) for controlling pressure in the ventilator circuit during inhalation and exhalation. For example, the ventilator may be connected to centralized sources of pressurized air and pressurized oxygen and may comprise one or more pressure regulating inspiratory valves for regulating the flow or pressure of gases delivered to the patient during inhalation. The regulating inspiratory valves function to regulate flow so that respiratory gases having a desired concentration of oxygen are supplied to the patient at a desired pressure and rate. Additionally, the ventilator may comprise an exhalation valve, which controls the pressure and rate of gases released from the patient circuit during exhalation (i.e., exhaled gases) and/or inhalation (i.e., in the case of inspiratory pressure overshoot). Ventilators capable of operating independently of external sources of pressurized air are also available.

Patients may require respiratory support for a number of reasons. For example, patients may have healthy lungs, but may be ventilated during an invasive surgery. Alternatively, patients may require respiratory support because they are unable to breathe independently because their lungs are diseased or injured. Diseases affecting the lungs include Chronic Obstructive Pulmonary Disease (COPD), emphysema, pneumonia, lung cancer, pulmonary embolism, etc. In many cases, oxygen exchange may be increased if a minimum, positive pressure of gases (i.e., PEEP) is maintained in the alveoli. Moreover, in some cases, if a minimum amount of pressure is not maintained in the lungs, the alveoli may collapse and become adherent at the end of exhalation and then be torn open during the next inhalation—causing additional damage to the lungs. Accordingly, PEEP is often prescribed for ventilated patients.

As discussed above, ventilated patients are more comfortable when the delivered volume of inspired gases is exhaled against the least resistance possible. Indeed, much of the resistance to exhalation is due to the exhalation valve itself. However, allowing exhaled gases to escape in an unregulated manner may allow the pressure in the patient's lungs to fall below PEEP. As such, embodiments described herein provide for regulating the exhalation valve to quickly release pressure in the patient circuit, which minimizes resistance and increases patient comfort, while at the same time regulating the exhalation valve to prevent PEEP undershoot in the lungs.

FIG. 1 is a diagram illustrating an embodiment of an exemplary ventilator 100 connected to a human patient 150. Ventilator 100 includes a pneumatic system 102 (also referred to as a pressure generating system 102) for circulating breathing gases to and from patient 150 via the ventilation tubing system 130, which couples the patient 150 to the pneumatic system 102 via an invasive (e.g., endotracheal tube, as shown) or a non-invasive (e.g., nasal mask) patient interface 180.

Ventilation tubing system 130 (or patient circuit 130) may be a two-limb (shown) or a one-limb circuit for carrying gases to and from the patient 150. In a two-limb embodiment, a fitting, typically referred to as a "wye-fitting" 170, may be provided to couple a patient interface 180 (as shown, an endotracheal tube) to an inspiratory limb 132 and an expiratory limb 134 of the ventilation tubing system 130.

Pneumatic system 102 may be configured in a variety of ways. In the present example, pneumatic system 102 includes an expiratory module 108 coupled with the expiratory limb 134 and an inspiratory module 104 coupled with the inspiratory limb 132. Compressor 106 or other sources) of pressurized gases (e.g., air, oxygen, and/or helium) is coupled with inspiratory module 104 and the expiratory module 108 to provide a gas source for ventilatory support via inspiratory limb 132.

The pneumatic system 102 may include a variety of other components, including mixing modules, valves, sensors, tubing, accumulators, filters, etc. Controller 110 is operatively coupled with pneumatic system 102, signal measurement and acquisition systems, and an operator interface 120 that may enable an operator to interact with the ventilator 100 (e.g., change ventilator settings, select operational modes, view monitored parameters, etc.). Controller 110 may include memory 112, one or more processors 116, storage 114, and/or other components of the type commonly found in command and control computing devices. In the depicted example, operator interface 120 includes a display 122 that may be touch-sensitive and/or voice-activated, enabling the display 122 to serve both as an input and output device.

The memory 112 includes non-transitory, computer-readable storage media that stores software that is executed by the processor 116 and which controls the operation of the ventilator 100. In an embodiment, the memory 112 includes one or more solid-state storage devices such as flash memory chips. In an alternative embodiment, the memory 112 may be mass storage connected to the processor 116 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 116. That is, computer-readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

The inspiratory module 104 determines the pressure of gases delivered during inspiration. The expiratory module 108 determines the pressure of gases in the patient circuit during exhalation. In one embodiment, the inspiratory module 104 and the expiratory module 108 determine the pressures during ventilation by controlling valves and/or gas flow within the ventilator 100. According to embodiments, pressure in the patient circuit reaches a maximum toward the end of inhalation (e.g., peak inspiratory pressure). Thereafter, as the patient begins to exhale, pressure is released from patient's lungs via the patient circuit based on a pressure gradient between the patient's lungs and ambient atmospheric pressure (about 0 cm $H_2O$). According to embodiments, pressure in the patient circuit may be regulated during exhalation by controlling the extent to which the exhalation valve opens or closes (i.e., regulating the rate at which gases are released from the system). For example, when the exhalation valve is opened to a greater extent, gases are allowed to escape more quickly from the patient circuit (reducing pressure in the patient circuit more quickly). Alternatively, when the exhalation valve is opened to a lesser extent, gases are allowed to escape less quickly from the patient circuit (reducing pressure in the patient circuit more slowly).

According to embodiments, pressure in the patient circuit may be regulated during the entire period of exhalation, such as the amount of pressure released per second or millisecond of the exhalation time period. According to further embodiments, the inspiratory module 104 and the expiratory module 108 may determine the pressures during ventilation by sending instructions (also known as a control commands) to the controller 110, which regulates the valves to control gas flow into or out of the patient circuit during ventilation.

According to embodiments, the exhalation valve in modern mechanical ventilators acts as a variable flow resistor during exhalation. As such, it can cause an increase in the imposed expiratory resistance placed upon the patient which leads to an increased work-of-breathing. As used herein, the term "work-of-breathing" refers to the effort exerted by the patient to inspire and/or exhale gases. Resistance may be reduced by opening the valve to a greater extent and allowing gases to be released from the patient circuit more quickly. However, as specified above, the exhalation valve is regulated such that pressure in the patient's lungs does not fall below PEEP. Moreover, the exhalation valve is regulated to prevent undesired oscillatory behavior of the pressure and flow in the patient circuit. For example, oscillatory behavior can result from nonlinearities of the pneumatic characteristics of the exhalation valve, high bandwidth of the control command, limitations of the sample rate of the control system, and latency of the real-time control command, etc.

In an effort to decrease resistance while preventing PEEP undershoot, systems and methods described herein utilize an expiratory module 108 that functions based on a time-variant expiratory pressure target during exhalation to ensure a faster exhalation time without allowing an undershoot in the lung pressure. Furthermore, systems and methods described herein utilize art exhalation valve control command based on results from an initialization to attenuate the oscillations in pressure and flow at the exhalation valve based on an individual patient. Moreover, systems and methods herein utilize feedback control to fine-tune the expiratory pressure target in order to achieve and maintain PEEP.

Figure 2A:
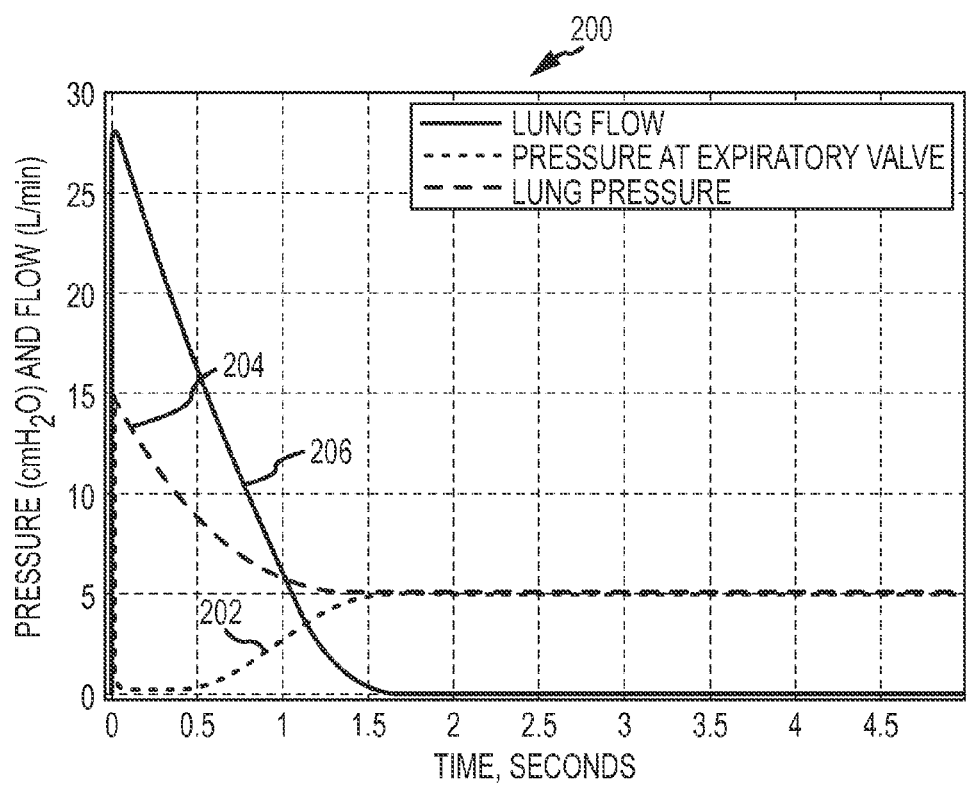
FIGS. 2A and 2B are graphs illustrating two embodiments of pressure and flow trajectories during exhalation of an exemplary patient on a ventilator.
Figure 2B:
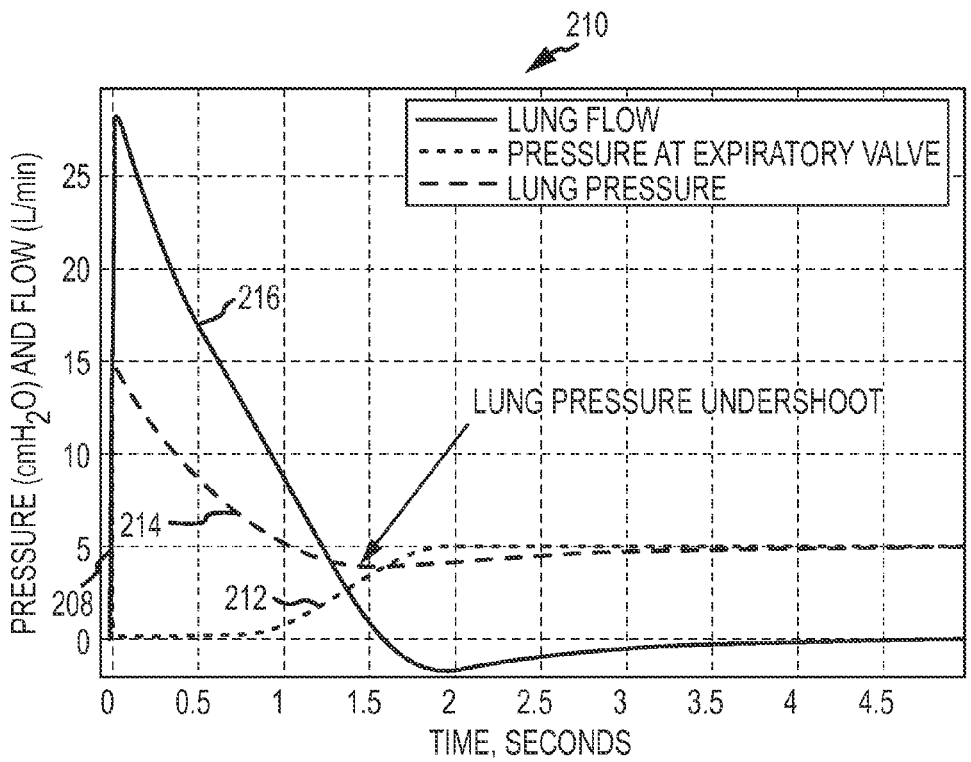

FIGS. 2A and 2B are graphs illustrating two embodiments of pressure and flow trajectories during exhalation of an exemplary patient on a ventilator. More specifically, FIG. 2A is a graph 200 showing an exhalation valve pressure trajectory 202, a lung pressure trajectory 204, a lung flow trajectory 206, and a desired PEEP level 208 at the lung. FIG. 2B is a graph 210 showing an exhalation valve pressure trajectory 212, a lung pressure trajectory 214, and a lung flow trajectory 216. In general, graphs 200 and 210 are exemplary embodiments of pressure and flow trajectories based on differing time constants generated by the ventilator.

The graph 200 shows the ideal pressure and flow trajectories of the patient during exhalation. As shown, the desired PEEP level 208, 5 $cmH_2O$, is reached at the end of exhalation by the lung pressure trajectory 204, without undershoot. Furthermore, though the exhalation valve pressure trajectory 202 undershoots the desired PEEP level 208 for approximately 1.5 seconds, the exhalation valve pressure trajectory 202 eventually stabilizes at the desired PEEP level 208, in the ideal amount of time to ensure that the lung pressure trajectory 204 does not undershoot PEEP. This ideal time is known as the tau time constant, and can be altered by the ventilator to adjust the lung pressure trajectory 204.

As shown in the graph 200, the pressure trajectories are more aggressive than modern mechanical ventilators. The exhalation valve pressure trajectory 202 initially drops to a reference value of 0 $cmH_2O$, instead of the desired PEEP level 208. By changing the reference pressure, the exhalation time is decreased substantially, as shown by the lung pressure trajectory 204. However, because the exhalation time decreases, the time constant is especially important to monitor so that there is no undershoot of the lung pressure.

FIG. 2B provides graph 210, which illustrates one embodiment in which lung pressure undershoot may occur. As shown, in the graph 210, the time it takes for the exhalation valve pressure trajectory 212 to achieve the desired PEEP level is almost 2 seconds, instead of 1.5 seconds in the graph 200. This minor yet substantial change in the time constant can negatively affect the lung pressure trajectory 214, as shown in the graph 210. As illustrated, the lung pressure trajectory 214 experiences PEEP undershoot.

Furthermore, the increased time constant also affects the lung flow trajectory 216. In comparison to the lung flow trajectory 206 of the graph 200, the lung flow trajectory 216 achieves stabilization in a far greater amount of time. In some patients, this can translate into greater discomfort and negative oscillations. Thus, the graphs 200 and 210 demonstrate that a more aggressive pressure trajectory can be utilized during exhalation, as long as, certain variables, such as the time constant, are calibrated on a patient-by-patient basis.

In general, this disclosure describes embodiments that utilize the concept of a more aggressive initial pressure reference as part of a modified exhalation valve control command provided to the controller 110. The exhalation valve control command determines the opening of the exhalation valve, and thus, the amount of time needed for gas to be exhaled by the patient 150. More specifically, the modified exhalation valve control command is developed through an initialization period in which several command values may be trained utilizing the more aggressive pressure trajectory discussed above. Next, ventilation is delivered based on the values trained in the initialization period with frequent monitoring of pressure and flow to ensure stability.

Figure 3:
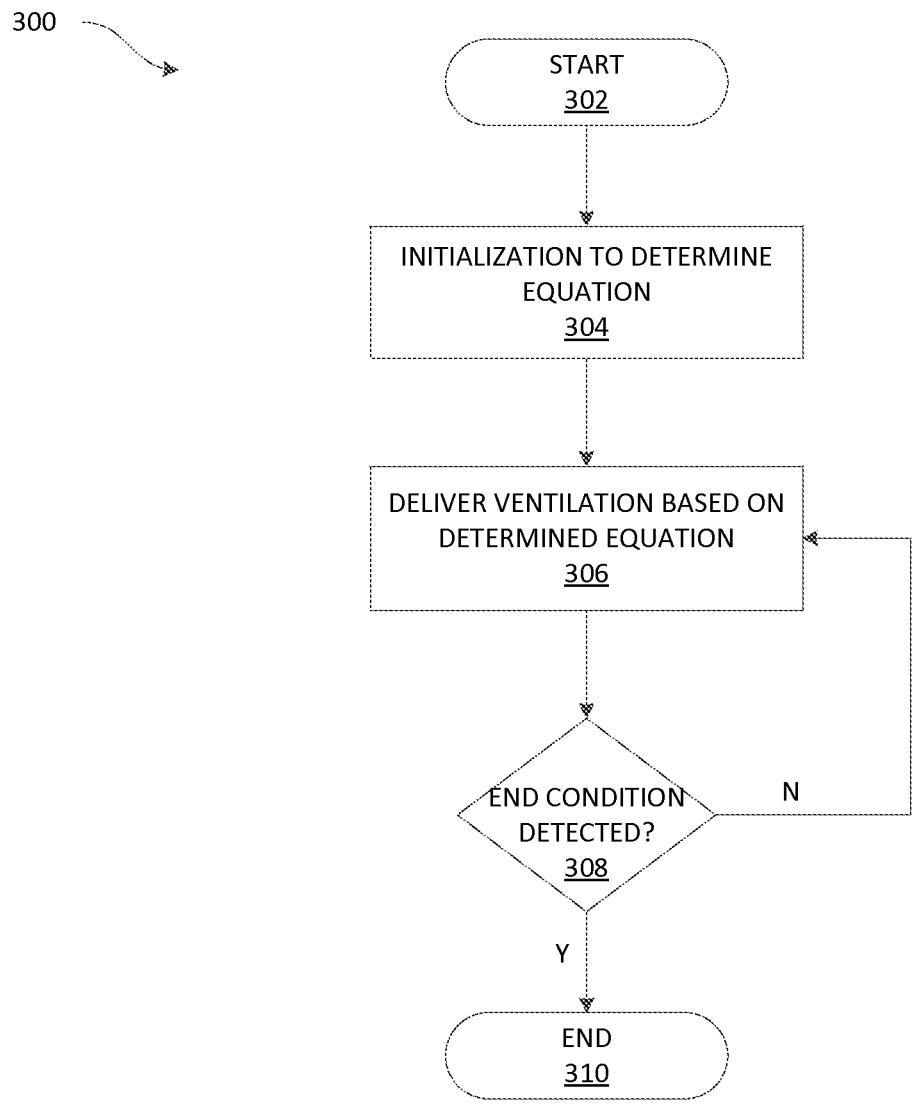
FIG. 3 illustrates an embodiment of a method for controlling exhalation during ventilation of a patient on a ventilator.

FIG. 3 illustrates an embodiment of a method 300 for controlling exhalation during ventilation of a patient on a ventilator, such as the ventilator 100. The method 300 includes an initiation operation 302, an initialization operation 304, a ventilation delivery operation 306, an end condition determination operation 308, and an end operation 310.

As illustrated, method 300 begins at the start of ventilation (operation 302). The ventilator 100 then moves to the initialization operation 304 in which the ventilator 100 determines initial values that are later used for a control command that is sent to the controller 110. Specifically, during the initialization operation 304, the ventilator 100 receives a predetermined clinician-inputted desired PEEP-level. Based on this information, and the individual characteristics of the patient, the ventilator 100 determines the appropriate reference pressure, as discussed above in relation to FIGS. 2A and 2B. Based on this reference pressure, the controller 110 determines a pressure for a first number of cycles of breaths. For example, in some embodiments, the ventilator 100 may monitor the lung pressure trajectory and the exhalation valve pressure trajectory of the patient 150 during the first two cycles of breath. In other embodiments, the ventilator 100 may monitor these pressures of the patient 150 during more or less cycles of breath.

During the initialization operation 304, the controller 110 determines minimum and steady-state values ($u_0$ and $u_{ss}$) (706 and 710, respectively, in FIG. 7) of the exhalation valve control command during these first cycles of breath and ensures that these values remain stable during each breath of the initialization operation 304. Through this initialization period, values may be trained differently for different patients, based on specifics of each patient. Various factors may alter the values based on the patient's body. For example, such factors may include, but are not limited to, the patient resistance and compliance due to patient physiology, such as the size of the lungs, the health status of the patient (i.e., any diseases or medical conditions), health risks associated with the patient, gender, age, or any other physiological factors that may affect resistance and/or compliance of the lungs.

Figure 7:
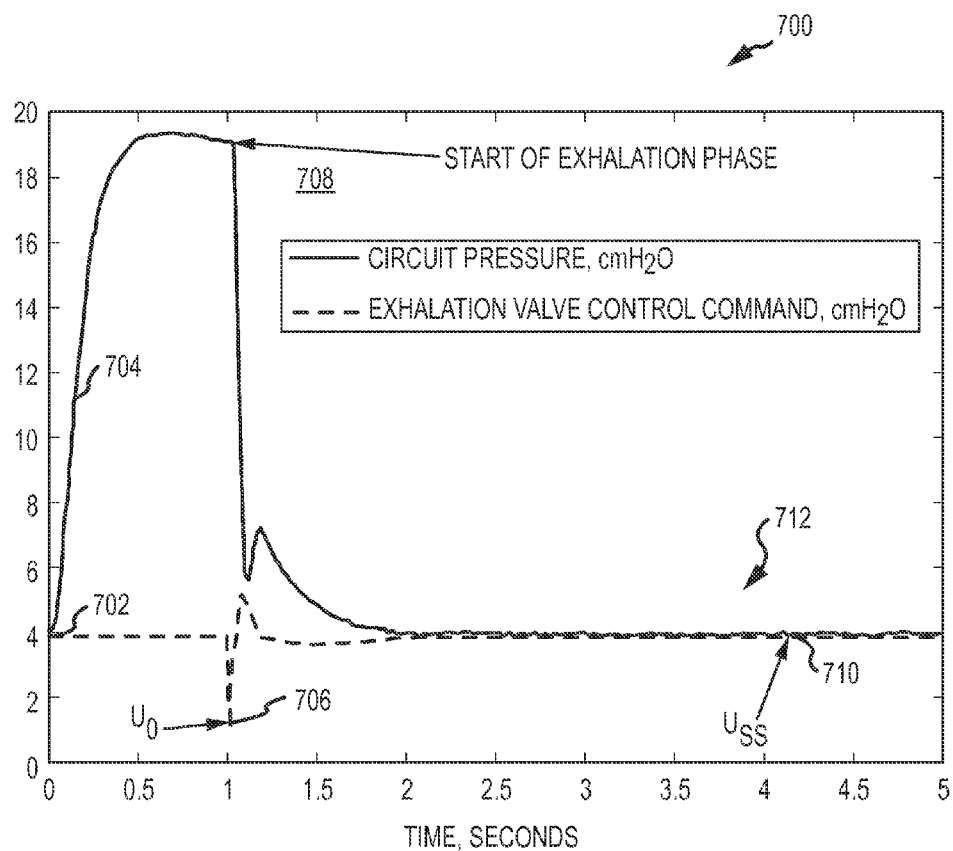
FIG. 7 is a graph illustrating one embodiment of circuit pressure and exhalation valve control command during each breath of the initialization operation 304 of FIG. 3.

The minimum ($u_0$) and steady-state ($u_{ss}$) values 706,710 are illustrated in FIG. 7. A graph 700 depicts an exhalation valve control command 702 and a circuit pressure 704 during a breath. As shown, the minimum value ($u_0$) 706 is the minimum value of the exhalation valve control command, which occurs at the initiation 708 of the exhalation phase. The steady state value ($u_{ss}$) 710 is a steady-state value of the exhalation valve control command during the steady-state period 712 of the exhalation phase (i.e., during the later portion of exhalation when the circuit pressure 704 has stabilized). During the initialization operation 304, the controller 110 determines these values over a predetermined number of initial exhalation cycles.

Upon determining $u_0$ and $u_{ss}$, the ventilator 100 begins the ventilation delivery operation 306, where ventilation continues over one or more breaths and, during exhalation, the exhalation valve is controlled based on the control command. Specifically, the initial values, $u_0$ and $u_{ss}$, determined from the initialization operation 304 are utilized to develop a modified exhalation valve control command. To determine the exhalation valve control command ($u(t_k)$) during ventilation delivery operation 306, the initial values ($u_{ss}$, $u_0$) are inputted into the following equations:

$$u(t_k)=(u_{ss}-u_0)*(1-\exp(-t_k/tau))+u_0; \text{ where}$$

$$tau=\text{sum}*(\text{sample period})/(u_{ss}-u_0); \text{ and where}$$

$$\text{sum}=\text{sum}+u_{ss}-u_0.$$

In the above equations, the tau represents the time constant and the sample period is the amount of breath cycles in the initialization operation 304. Upon inputting the known variables after the initialization operation 304, the ventilation delivery operation 306 begins and during each exhalation phase, the exhalation valve is controlled based on the control command signal (u), which remains a function of time ($t_k$).

The ventilator 100 continues to control the exhalation valve based on the above exhalation control command until the end condition detection operation 308 detects an end condition. Examples of end conditions include a change in the mode setting, a change in clinician-inputted values, a disconnection of the ventilator, an alarm setting, an operation failure, an occurrence of apnea, or the like. If an end condition is not detected by operation 308, the ventilator 100 continues to ventilate the patient and control the exhalation valve during exhalation based on the control command. However, if an end condition is detected by operation 308, the ventilator 100 discontinues ventilation and terminates at the end operation 310.

Figure 4:
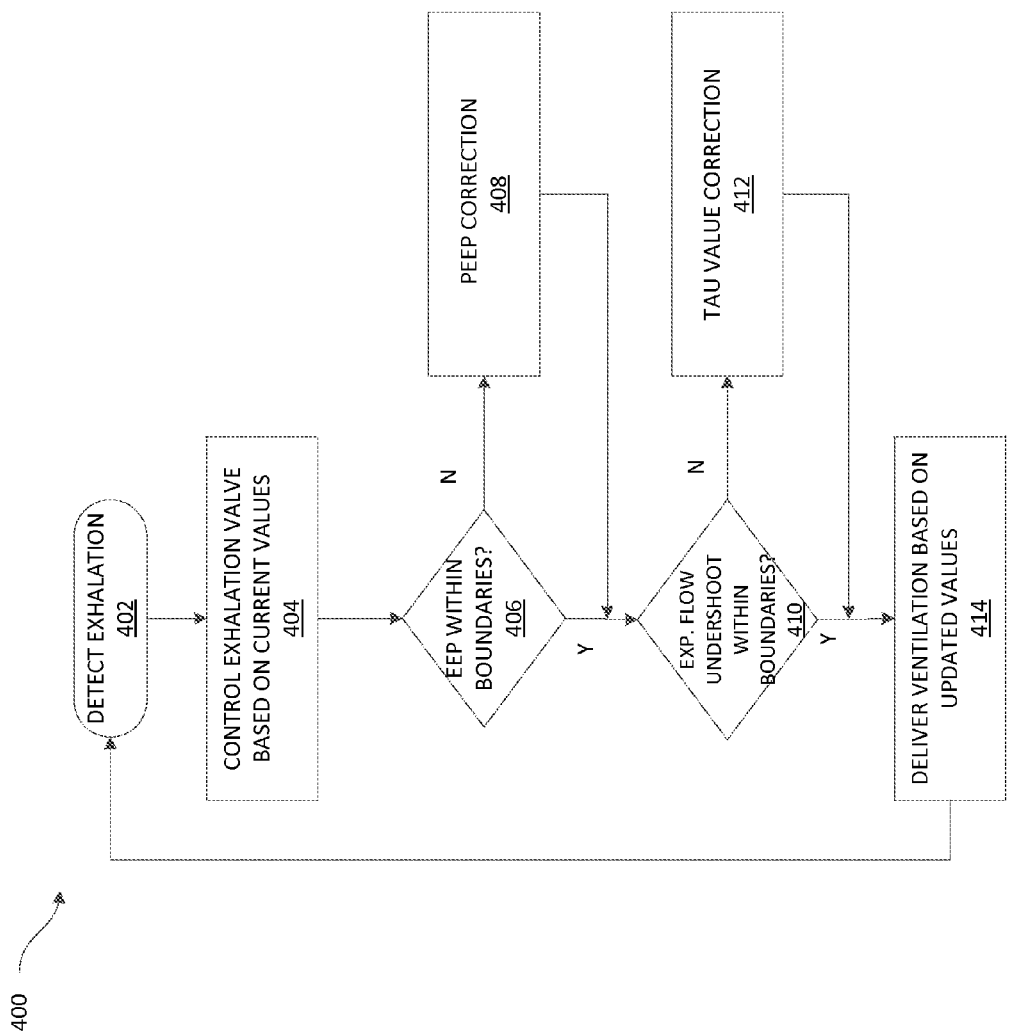
FIG. 4 illustrates one embodiment of operation 306 of FIG. 3.

FIG. 4 illustrates an embodiment of what occurs during the ventilation delivery operation 306 of the method 300. Specifically, FIG. 4 illustrates a method 400 for controlling the opening of the exhalation valve, and thereby the exhalation gasses released, during the exhalation phase.

The method 400 begins upon the detection of exhalation at an operation 402. Upon detecting exhalation, the method 400 delivers ventilation based on the control command signal $u(t_k)$ that was determined during the initialization operation 304. During each exhalation, the method 400 controls the exhalation valve and monitors the stability and consistency of the pressure and flow from one exhalation to the next. This ensures a smoother exhalation control command, and thus, fewer undesired oscillations experienced by the patient.

For example, upon detecting exhalation at operation 402, the ventilator controls the exhalation valve based on the current values at operation 404. More specifically, the ventilator 100 determines whether the measured end exhalation pressure ("EEP") of the exhalation valve is within some predetermined range (operation 406). The predetermined range may be any range determined by the controller 110 or a clinician prior to exhalation based on factors varying based on each patient, such as, the size of the lungs, the health status of the patient, health risks associated with the patient, or any other individual factors that may affect ventilation. For example, the range may be determined based on a maximum allowable threshold difference between the EEP and the desired PEEP level. The EEP is determined by pressure sensors positioned in the pneumatic system 102, for example, at the exhalation valve.

Upon comparing the EEP measurements with the predetermined allowable range, the operation 406 determines whether the EEP is at an acceptable level. If the ventilator 100 determines that the EEP falls outside of the predetermined range, the method 400 initiates a PEEP correction operation 408. In general, the PEEP correction operation 408 monitors the pressure trajectory of the exhalation valve, and adjusts the trajectory so that the EEP of the exhalation valve falls within the predetermined range. The determination operation 406 and the PEEP correction operation 408 are discussed in greater detail below in reference to FIG. 5.

Additionally, the method 400 monitors the expiratory flow undershoot at an operation 410. At operation 410, the ventilator 100 determines whether the expiratory flow of the exhalation valve is under a predetermined threshold. It is important to note that the predetermined threshold of the expiratory flow undershoot is different than the predetermined range discussed above in relation to the EEP threshold. Also, the predetermined threshold of the expiratory flow undershoot may be any threshold determined by the controller 110 or a clinician prior to exhalation based on the factors discussed above. The expiratory flow is measured by sensors positioned in the pneumatic system 102, for example, at the exhalation valve. From this measurement, the controller 110 can determine the expiratory flow undershoot and then compare this measurement to the predetermined threshold.

If the ventilator 100 determines that the expiratory flow undershoot at the exhalation valve is above the predetermined threshold, the method 400 initiates a tau value correction operation 412. In general, at operation 412, the tau value utilized in the exhalation valve control command ($u(t_k)$), is adjusted so that the expiratory flow undershoot is regulated under the predetermined threshold. Thus, the operation 412 adjusts the control command that is sent to the controller 110 which alters the positioning of the exhalation valve. The determination operation 410 and the tau value correction operation 412 is discussed in greater detail in relation to FIG. 6.

If, on the other hand, the ventilator 100 determines that the expiratory flow undershoot at the exhalation valve is under the predetermined threshold, the ventilator 100 continues to control the exhalation valve based on any updated values that may have been corrected during either the PEEP correction operation 408 or the tau value correction operation 412. If no values were adjusted, the operation 414 continues to control the exhalation valve based on values from the previous breath cycle until the end of the current exhalation. Upon beginning the subsequent exhalation, the method 400 begins again at operation 402.

Figure 5:
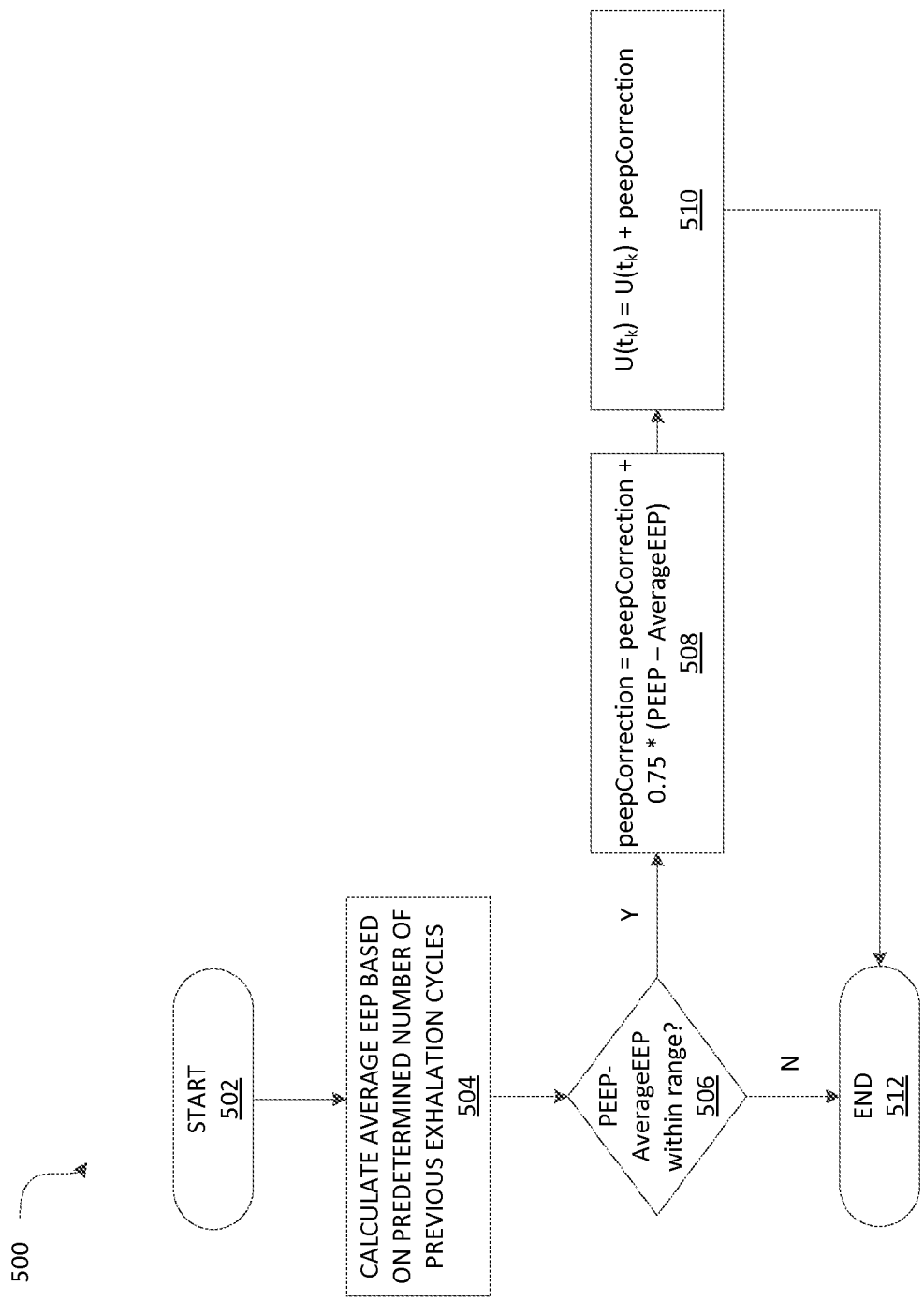
FIG. 5 illustrates one embodiment of operations 406 and 408 of FIG. 4.

FIG. 5 illustrates an embodiment of what occurs during the EEP determination operation 406 and the PEEP correction operation 408 of the method 400. Specifically, FIG. 5 illustrates a method 500 for determining the EEP of the exhalation valve and updating the pressure trajectory of the exhalation valve during ventilation if necessary.

As illustrated, the method 500 begins at the start of exhalation (operation 502). The method 500 then enters an average EEP calculation operation 504. During the operation 504, the ventilator 100 calculates an average EEP based on a predetermined number of previous exhalations. For example, the calculation could be based on the past ten exhalations. In other embodiments, the predetermined number of previous exhalations could be any number deemed appropriate by a clinician or determined by the controller 110. For example, the calculation could be programmed so that initial calculation of the average EEP are based on fewer cycles of exhalation whereas later calculations of the average EEP are based on greater cycles of exhalation. The exact EEP measurements of each exhalation are measured by pressure sensors positioned on or around the exhalation valve and stored in the memory 112. At operation 504, the ventilator 100 utilizes the measurements stored in the memory 112 for a previous number of prior exhalations to determine the average EEP.

Upon determining the average EEP for the current exhalation, the method 500 determines how close the average EEP is to the clinician-inputted PEEP level at operation 506. This reference value is discussed in greater detail above in relation to the initialization operation 304 in FIG. 3. Specifically, the operation 506 calculates the difference between the clinician-inputted PEEP level and the average EEP. Next, the operation 506 determines whether the difference falls within a predetermined range based on the clinician-inputted PEEP level. For example, in some embodiments, the predetermined range may be between 0 and 0.25 $cmH_2O$. However, in other embodiments this range may vary based on the factors relating to the unique needs of individual patients, as discussed above.

If the operation 506 determines that the average EEP does not fall within the predetermined threshold, the method 500 moves to a peep correction operation 508. The peep correction operation 508 utilizes the following equation:

peepCorrection=peepCorrection+0.75*(PEEP−AverageEEP).

In the equation, PEEP is the clinician-inputted PEEP level, AverageEEP is the average EEP that is determined in the operation 504, and peepCorrection is the correction, if any, that was made in the previous exhalation cycle. If no correction was made in the previous exhalation cycle, peepCorrection=0.

After determining the peepCorrection value in operation 508, the method 500 moves to operation 510 in which the peepCorrection value is utilized to alter the control command signal that is sent to the controller 110 to alter the position of the exhalation valve. Specifically, the operation 508 utilizes the following equation to alter the control command ($u(t_k)$):

$u(k_k)=u(t_k)_{PREVIOUS}$+peepCorrection.

In this equation, as illustrated, $u(t_k)_{PREVIOUS}$ is the control command that was utilized in the previous exhalation cycle.

Upon altering the control command ($u(t_k)$), the method 500 terminates at an end operation 512. The method 500 is called again to monitor the average EEP of the exhalation valve at the start of the next exhalation cycle.

Figure 6:
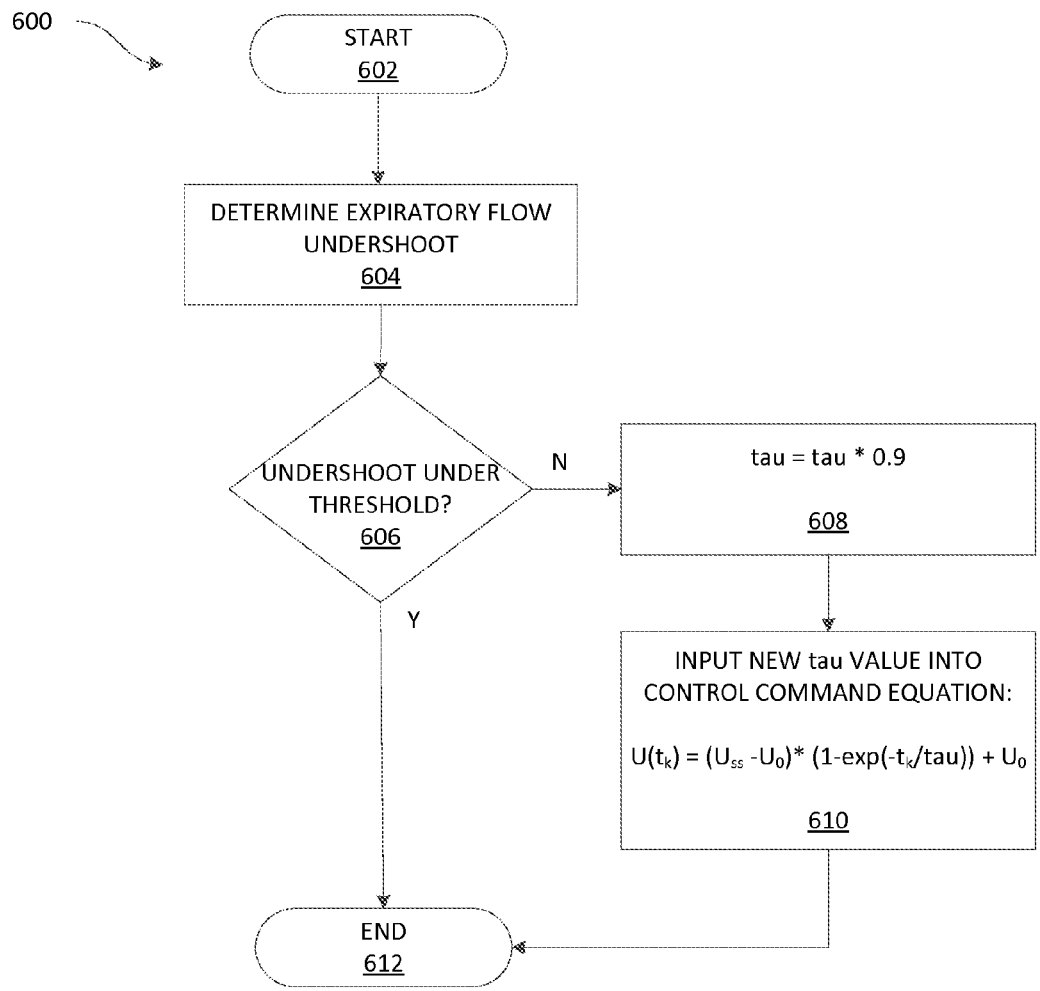
FIG. 6 illustrates one embodiment of operations 410 and 412 of FIG. 4.

FIG. 6 illustrates an embodiment of what occurs during the expiratory flow undershoot determination operation 410 and the tau value correction operation 412 of the method 400. Specifically, FIG. 6 illustrates a method 600 for determining the expiratory flow undershoot and updating the tau value, and thus, the control command of the exhalation valve during ventilation if necessary.

As illustrated, the method 600 begins at an initial point 602. The method 600 then enters an expiratory flow undershoot operation 604. At operation 604, the ventilator 100 measures the expiratory flow of the exhalation valve through flow sensors positioned on or around the exhalation valve. Based on these measurements, the ventilator 100 determines whether there is an undershoot in the expiratory flow and, if so, the amount of undershoot present.

Upon determining the undershoot, the method 600 moves to an operation 606 where the ventilator 100 compares the measured undershoot from operation 604 to a predetermined threshold. For example, in some embodiments, the predetermined threshold may be 0.2 L/min. However, in other embodiments, the predetermined threshold may vary based on the factors that differ for individual patients, discussed above. If it is determined that the measured undershoot falls below the predetermined threshold, the method 600 will terminate at an end operation 612. However, if the measured undershoot falls above the predetermined undershoot flow threshold, the method 600 moves to a tau correction operation 608.

In an embodiment, the tau correction operation 608 updates the time constant, tau, by a fixed amount, in this case a reduction of 10%, utilizing the following equation:

tau=tau*0.9.

In the equation, tau is the value of tau from the previous exhalation cycle. In an alternative embodiment, the time constant may be adjusted based on the amount of undershoot detected, such as by a proportional amount based on the relative difference between the measured undershoot and the threshold. Other factors could also be used to determine the amount to adjust the undershoot including measured EEP, PEEP, and/or patient characteristics.

Based on the tau correction operation 608, the new tau value is then utilized to update the control command signal that is sent to the controller 110. This occurs in an operation 610. The updated tau value is inputted into the original control command equation, as discussed in relation to FIG. 3, shown below:

$u(t_k)=(u_{ss}-u_0)*(1-\exp(-t_k/tau))+u_0$.

In the equation, the updated tau value is inputted into the control command equation which is sent to the controller 110. Based on this new control command, the opening of the exhalation valve is adjusted so that the expiratory flow undershoot falls within the appropriate threshold. Upon updating the control command, the method 600 terminates at the end operation 612.

Those skilled in the art will recognize that the methods and systems of the present disclosure may be implemented in many manners and as such are not to be limited by the foregoing exemplary embodiments and examples. In other words, functional elements being performed by a single or multiple components, in various combinations of hardware and software or firmware, and individual functions, can be distributed among software applications at either the client or server level or both. In this regard, any number of the features of the different embodiments described herein may be combined into single or multiple embodiments, and alternate embodiments having fewer than or more than all of the features herein described are possible. Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, and those variations and modifications that may be made to the hardware or software or firmware components described herein as would be understood by those skilled in the art now and hereafter.

Numerous other changes may be made which will readily suggest themselves to those skilled in the art and which are encompassed in the spirit of the disclosure and as defined in the appended claims. While various embodiments have been described for purposes of this disclosure, various changes and modifications may be made which are well within the scope of the present invention. Numerous other changes may be made which will readily suggest themselves to those skilled in the art and which are encompassed in the spirit of the disclosure and as defined in the appended claims.

What is claimed is:

1. A method for controlling exhalation during ventilation of a patient on a ventilator, the method comprising:
   determining a control command for an exhalation valve, wherein the control command targets a pressure at the exhalation valve between a minimum pressure and a steady-state pressure for a period of time;
   controlling the exhalation valve based on the control command during one or more exhalation cycles;
   monitoring an end exhalation pressure and a flow undershoot during the one or more exhalation cycles;
   comparing the end exhalation pressure to a predetermined pressure range;
   comparing the flow undershoot to a predetermined flow threshold; and
   based on the comparing, updating the control command in order to maintain a positive-end expiratory pressure (PEEP) at the end of the one or more exhalation cycles.

2. The method of claim 1, wherein the pressure is lower than the PEEP.

3. The method of claim 1 wherein the period of time is two breath cycles.

4. The method of claim 1, wherein the control command is determined by an equation:

$$u(t_k) = (u_{ss} - u_0) * (1 - \exp(-t_k/tau)) + u_0,$$

wherein tau=sum*(the predetermined number of breath cycles)/$(u_{ss} - u_0)$,
wherein sum=sum+$u_{ss} - u_0$,
wherein $t_k$ is an exhalation time,
wherein $u_0$ is the minimum pressure during the period of time, and
wherein $u_{ss}$ is the steady-state pressure during the period of time.

5. The method of claim 1 wherein comparing the end exhalation pressure to the predetermined pressure range further comprises:
   determining an average end exhalation pressure based on the end exhalation pressures of a prior number of exhalation cycles; and
   determining whether the average end exhalation pressure falls outside of the predetermined pressure range.

6. The method of claim 5 wherein the prior number of exhalation cycles is 10.

7. The method of claim 5 wherein determining whether the average end exhalation pressure falls outside of the predetermined pressure range further comprises:
   calculating a difference between the average end exhalation pressure and the PEEP; and
   determining whether the difference falls outside of the predetermined pressure range.

8. The method of claim 1 wherein comparing the flow undershoot to the predetermined flow threshold further comprises:
   measuring an expiratory flow of the exhalation valve during the one or more exhalation cycles;
   determining the flow undershoot of the expiratory flow; and
   determining whether the flow undershoot falls under the predetermined flow threshold.

9. The method of claim 1 wherein the predetermined flow threshold is 0.2 L/min.

10. The method of claim 1 further comprising terminating control of the exhalation valve upon detection of an end condition.

11. A ventilator system, comprising:
   means for determining a control command for an exhalation valve, wherein the control command targets a pressure at the exhalation valve between a minimum pressure and a steady-state pressure for a period of time;
   means for controlling the exhalation valve based on the control command during one or more exhalation cycles;
   means for monitoring an end exhalation pressure and a flow undershoot during the one or more exhalation cycles;
   means for comparing the end exhalation pressure to a predetermined pressure range;
   means for comparing the flow undershoot to a predetermined flow threshold; and
   based on the comparing, means for updating the control command in order to maintain a positive-end expiratory pressure (PEEP) at the end of the one or more exhalation cycles.

12. A computer-readable medium having computer-executable instructions for performing a method controlling exhalation during ventilation of a patient on a ventilator, the method comprising:
   determining a control command for an exhalation valve, wherein the control command targets a pressure at the exhalation valve between a minimum pressure and a steady-state pressure for a period of time;
   repeatedly controlling the exhalation valve based on the control command during one or more exhalation cycles;
   repeatedly monitoring an end exhalation pressure and a flow undershoot during the one or more exhalation cycles;
   repeatedly comparing the end exhalation pressure to a predetermined pressure range;

repeatedly comparing the flow undershoot to a predetermined flow threshold; and based on the comparing, repeatedly updating the control command in order to maintain a positive-end expiratory pressure (PEEP) at the end of the one or more exhalation cycles.

13. The method of claim 12, wherein the pressure is lower than the PEEP.

14. The method of claim 12 wherein repeatedly comparing the end exhalation pressure to the predetermined pressure range further comprises:

repeatedly determining an average end exhalation pressure based on the end exhalation pressures of a prior number of exhalation cycles; and repeatedly determining whether the average end exhalation pressure falls outside of the predetermined pressure range.

15. The method of claim 14 wherein repeatedly determining whether the average end exhalation pressure falls outside of the predetermined pressure range further comprises:

repeatedly calculating a difference between the average end exhalation pressure and the PEEP; and repeatedly determining whether the difference falls outside of the predetermined pressure range.

16. The method of claim 12 wherein repeatedly comparing the flow undershoot to the predetermined flow threshold further comprises:

repeatedly measuring an expiratory flow of the exhalation valve during the one or more exhalation cycles;

repeatedly determining the flow undershoot of the expiratory flow; and repeatedly determining whether the flow undershoot falls under the predetermined flow threshold.

* * * * *